United States Patent [19]

De Bell Daniel

[11] Patent Number: 5,233,714
[45] Date of Patent: Aug. 10, 1993

[54] INFANT RESTRAINING DEVICE

[76] Inventor: Janice De Bell Daniel, 225 Kyle Rd., Winston-Salem, N.C. 27104

[21] Appl. No.: 883,893

[22] Filed: May 12, 1992

Related U.S. Application Data

[63] Continuation of Ser. No. 599,062, Oct. 17, 1990, abandoned.

[51] Int. Cl.⁵ .............................................. A47D 15/00
[52] U.S. Cl. ................................................ 5/655; 5/424; 128/873; 128/876
[58] Field of Search ............... 5/655, 424, 494, 498; 128/869, 871-873, 876

[56] References Cited

U.S. PATENT DOCUMENTS

| | | | |
|---|---|---|---|
| 2,569,627 | 10/1951 | Black | 5/497 |
| 2,589,708 | 3/1952 | Koster | 128/873 |
| 3,243,827 | 4/1966 | Kintner | 5/496 |
| 3,872,524 | 3/1975 | Hummel | 5/494 X |
| 3,987,505 | 10/1976 | Hickey | 5/494 X |
| 4,045,832 | 9/1977 | DiForti et al. | 5/496 |
| 4,144,602 | 3/1979 | Fernandes | 5/496 |
| 4,471,767 | 9/1984 | Guimond | 128/24 |
| 4,657,005 | 9/1987 | Williamson | 128/134 |
| 4,672,958 | 6/1987 | Garman | 128/873 |
| 4,703,530 | 11/1987 | Gusman | 5/497 |
| 4,745,926 | 5/1988 | Hlusko | 128/134 |
| 4,860,771 | 8/1989 | Burgos | 128/872 |
| 4,862,535 | 9/1989 | Roberts | 5/431 |
| 4,989,286 | 2/1991 | Tucker | 5/494 X |

FOREIGN PATENT DOCUMENTS

2615081 11/1988 France ................................ 5/424

Primary Examiner—Michael F. Trettel
Attorney, Agent, or Firm—Herbert J. Bluhm

[57] ABSTRACT

An improved infant restraining device that is adapted for use with a mattress or other infant-supporting structure and which is used for dealing with infants afflicted with gastroesophageal reflux comprises an elongated flexible sheet having opposing first and second ends, two opposing side edges each provided with a flared portion capable of being wrapped around respective opposing side edges of the mattress on which the device is placed and cooperating releasable attachment means associated with the first end of the flexible sheet and with each of the flared portions to permit the infant restraining device to be firmly anchored to one end of the mattress when the opposing flared portions are attached to the first end of the flexible sheet on the underside of the mattress. The second end of the flexible sheet is designed to engage the lower torso of an infant and to restrain movement of the infant even though the mattress to which the device is anchored may be inclined at angles up to 45 degrees.

13 Claims, 4 Drawing Sheets

INFANT RESTRAINING DEVICE

This is a continuation of co-pending application Ser. No. 07/599,062 filed on Oct. 17, 1990, now abandoned.

FIELD OF THE INVENTION

This invention relates to a device for holding an infant on an inclined surface in a relatively fixed position to control any gastroesophageal reflux that might be experienced by the infant.

BACKGROUND OF THE INVENTION

The ingestion of infant formula by newborn babies and other infants sometimes leads to life-threatening situations if the infant has gastroesophageal reflux (GER) caused by a weak esophageal sphincter which allows stomach contents to move back into the esophagus. GER can produce a vagal response leading to apnea or bradycardia. This problem with food being regurgitated (i.e., gastroesophageal reflux) is generally controlled by placing the infant on its stomach and on an inclined surface with the head being at a higher elevation than the torso of the infant. The elevated position of the infant's head tends to prevent regurgitation of the ingested food since the force of gravity will cause the contents of the stomach to move away from the esophageal opening and to the lower portion of the stomach. However, the inclined surface which supports the infant will allow the infant to slide sideways or downwardly unless an appropriate restraining device is used to hold the infant in the desired position.

A number of devices have been previously disclosed for dealing with the GER problem. For example, U.S. Pat. No. 4,657,005 discloses a harness arrangement in which shoulder straps and waist-encircling straps are used to hold the infant in place. The device is provided with anchor straps and anti-roll straps which are pinned to the mattress on which the device is placed or, alternatively, they are tied to nearly immovable objects which serve to restrict movement of the harness arrangement. Such means for anchoring are not entirely satisfactory because repeated pinnings to the mattress have a destructive effect on the mattress fabric over a period of time and any immovable objects to which the straps are tied may not be located in the most effective position.

Another device is disclosed in U.S. Pat. No. 4,745,926 which employs straps in conjunction with a diaper-shaped portion of the device and wherein the straps extend over the shoulders and are provided with tabs for pinning the straps to the infant's supporting mattress. The anchoring means in this design are also unsatisfactory for the same reason mentioned above, namely, the destructive effect that repeated pinnings have on the mattress fabric. Moreover, the device is somewhat cumbersome to use, it is uncomfortable for the infant and it may interfere with quick removal of an infant in an emergency. Also, the close proximity of other shoulder straps to the infant's head make the straps vulnerable to frequent soiling by vomit.

Other infant restraint devices which employ anchoring straps designed for attachment to side rails of a crib include U.S. Pat. No. 2,566,046 and U.S. Pat. No. 4,672,958 but those devices are generally restricted to use in cribs that have side rail uprights or similar structural elements to which anchoring straps can be attached.

In U.S. patent application Ser. No. 07/430,181 filed Nov. 1, 1989, an improved infant restraining device is disclosed which does not rely on pinning the device to a supporting mattress for anchoring purposes or on attaching straps to side rails. Instead, the device employs a pocket associated with one end of the restraint device that is designed to envelop snugly one end of the supporting mattress so that the device is held in a relatively fixed position. While that design is effective and easy to use, it requires a preformed pocket having an opening that is sized to accommodate one end of the mattress. The nursery settings in hospitals typically include cribs and mattresses of different sizes so that restraining devices relying on mattress-engaging pockets for anchoring purposes must be provided with pockets having sizes designed to accommodate the various sized mattresses. It is rather inconvenient and time-consuming to maintain an inventory of restraint devices sorted according to pocket size when the devices are laundered and returned to a nursery supply room prior to re-use of the devices.

SUMMARY OF THE INVENTION

The improved infant restraining device disclosed herein has for its primary object the capability of being used with different sized mattresses without any sacrifice in effectiveness. This device also provides a restraint design that is easier to use and is, therefore, more efficient than previously disclosed restraint devices intended for use with supporting mattresses. Additionally, the infant-restraining portion of the device may be easily disengaged to permit quick removal of an infant in any emergency situations.

This invention comprises an improved infant restraining device adapted for use with an infant-supporting mattress that is maintained in an inclined position ranging up to approximately 45 degrees. The invention includes an elongated flexible sheet having opposing first and second ends with one surface of the flexible sheet being designated as the mattress-contacting surface and the opposite surface of the sheet being designated as the infant-contacting surface. The first end of the flexible sheet is designed to wrap around one end of a supporting mattress with a sufficient length of the first end extending along the underside of the mattress for anchoring purposes. The second end of the flexible sheet is designed to receive an infant placed on the mattress-supported restraining device. The flexible sheet is provided with opposing first and second side edges disposed between the first and second ends, a portion of each side edge intermediate the first and second ends of the flexible sheet being flared a sufficient amount to permit the opposing flared portions to wrap around the respective opposing sides of the supporting mattress and to extend along the underside of the mattress a sufficient distance so that the flared portions overlap portions of the length of the first end of the flexible sheet that extends along the underside of the mattress. The flared portions of the opposing first and second side edges as well as the portion of the first end that extends along the underside of the mattress are provided with means for releasably attaching the overlapping flared portions of the side edges to the first end of the flexible sheet extending along the underside of the mattress so that one end of the mattress is snugly enveloped, thereby anchoring the restraining device to the mattress. The second end of the elongated flexible sheet is provided with means for releasably attaching the second end of the sheet to a plurality of points on the sheet that are intermediate the first and second ends. Thus, when the second end of the sheet is directed between the legs of an infant placed on the infant-contacting surface and is brought into contact with the plurality of points intermediate the first and second ends, the lower torso of the infant is securely retained by the restraining device.

DETAILED DESCRIPTION OF THE INVENTION

The improved infant-restraining device disclosed herein is intended for use with an infant-supporting structure such as a mattress. The term "mattress" is intended to include any alternative structure that is capable of supporting the infant and of providing sufficient rigidity to anchor the infant-restraining device that is installed on one end of the mattress or alternative structure. Thus, the device may be used with a wide variety of commonly used equipment including isolettes, open cribs, open warmers and pediatric or bassinet size mattresses. The mattress, however, is not a part of the device disclosed herein even though the mattress and device are in direct contact during use.

It should also be noted that a mattress used with the present invention to treat an infant afflicted with gastroesophageal reflux will be provided with means for maintaining the mattress in an inclined position. The particular means used to maintain the inclined position of the mattress is not a critical factor as far as this invention is concerned and may include any commonly used techniques for positioning the mattress alone or positioning the entire crib or other structure in which the mattress is placed. Nevertheless, the means for adjusting the mattress to a desired inclined position constitutes an essential part of the method for treating infants with GER and it makes the presently disclosed device necessary due to the inclined position of the mattress.

In contrast to the infant restraining device disclosed in U. S. patent application Ser. No. 07/430,181, the presently disclosed invention does not rely on a preformed pocket for anchoring to a supporting mattress. Rather, this device is provided with releasable attaching means secured at strategic locations on the device so that one end of a supporting mattress may be snugly and partially enveloped by portions of the device.

Figure 1:
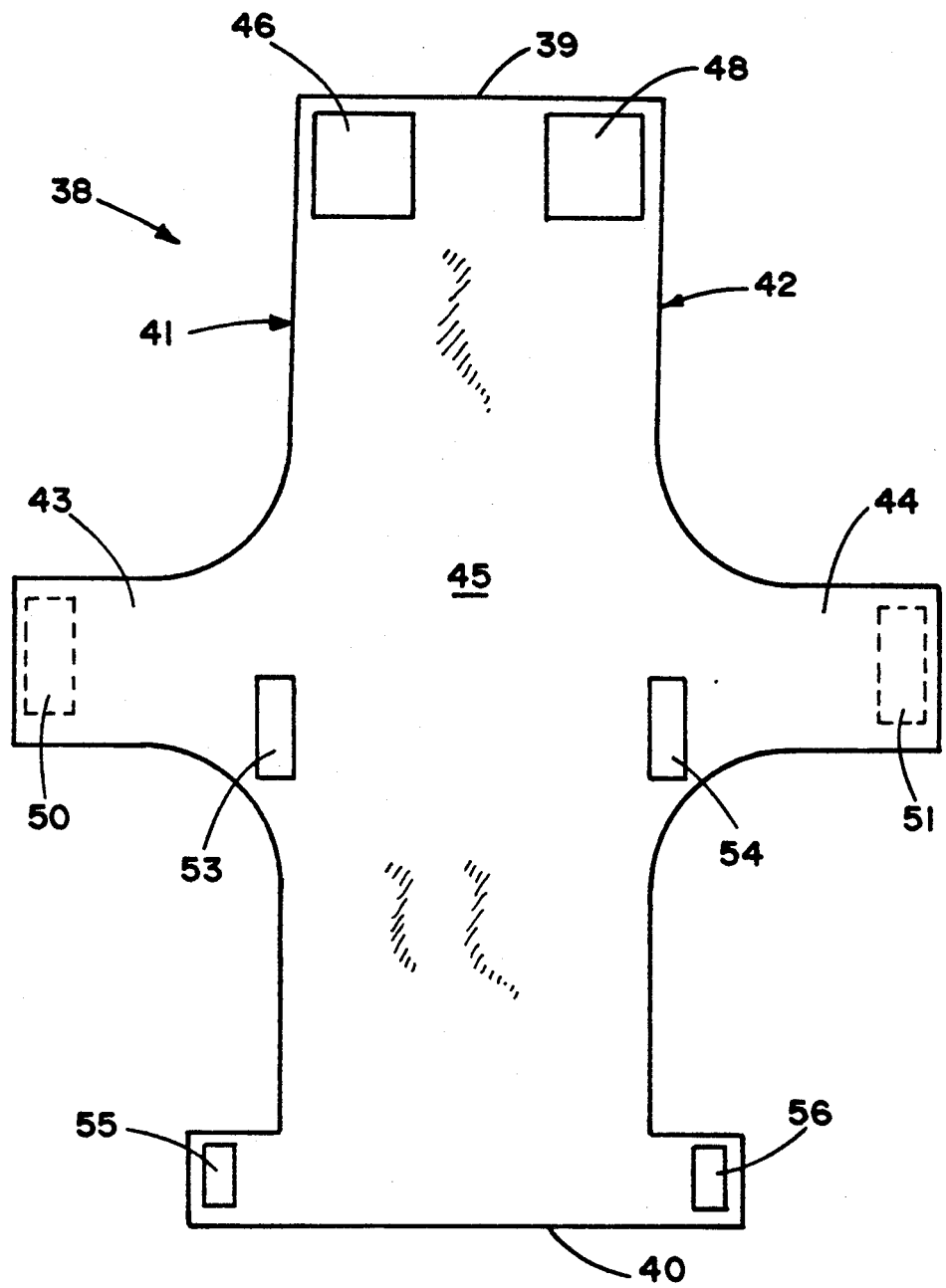
FIG. 1 is a top plan view of an embodiment of the invention disclosed herein.

One embodiment of the device is shown in FIG. 1 where flexible sheet 38 has opposing first and second ends 39 and 40, respectively. Disposed between ends 39 and 40 are opposing first and second side edges 41 and 42 which have portions 43 and 44 flared outwardly a sufficient amount to permit each flared portion to wrap around the opposing side edges of a supporting mattress and to extend a predetermined distance along the underside of the mattress. First end 39 is designed to wrap around one end of the supporting mattress, a length of end 39 extending along the underside of the mattress into the same area to which flared portions 43 and 44 extend. It is preferred that the width of the device adjacent to first end 39 (i.e., the distance between side edge 41 and side edge 42) be no greater than the width of the mattress on which it is to be installed in order to eliminate the need for dealing with excess flexible sheet material at the corners of the mattress when flared portions 43 and 44 and first end 39 are wrapped around one end of the supporting mattress. Except for the portions of end 39 and flared portions 43 and 44 which wrap around the top and side edges of the mattress, infant-contacting surface 45 faces substantially upwardly when the device is installed on a mattress. Secured to surface 45 adjacent to end 39 are patches 46 and 48 of releasable attachment means. Similar patches 50 and 51 of releasable attachment means are secured to the underside, or mattress-contacting surface, of flexible sheet 38 on flared portions 43 and 44. Patches 46 and 50 together with patches 48 and 51 cooperate to join flared portions 43 and 44 to end 39 as the device engages and is anchored to one end of the supporting mattress. Second end 40 of flexible sheet 38 is provided with patches 55 and 56 of releasable attachment means which cooperate with patches 53 and 54, respectively, of releasable attachment means to hold the lower torso of an infant placed in the restraining device by bringing end 40 between the legs of the infant and the cooperating patches of releasable attachment means into contacting relationship.

Figure 2:
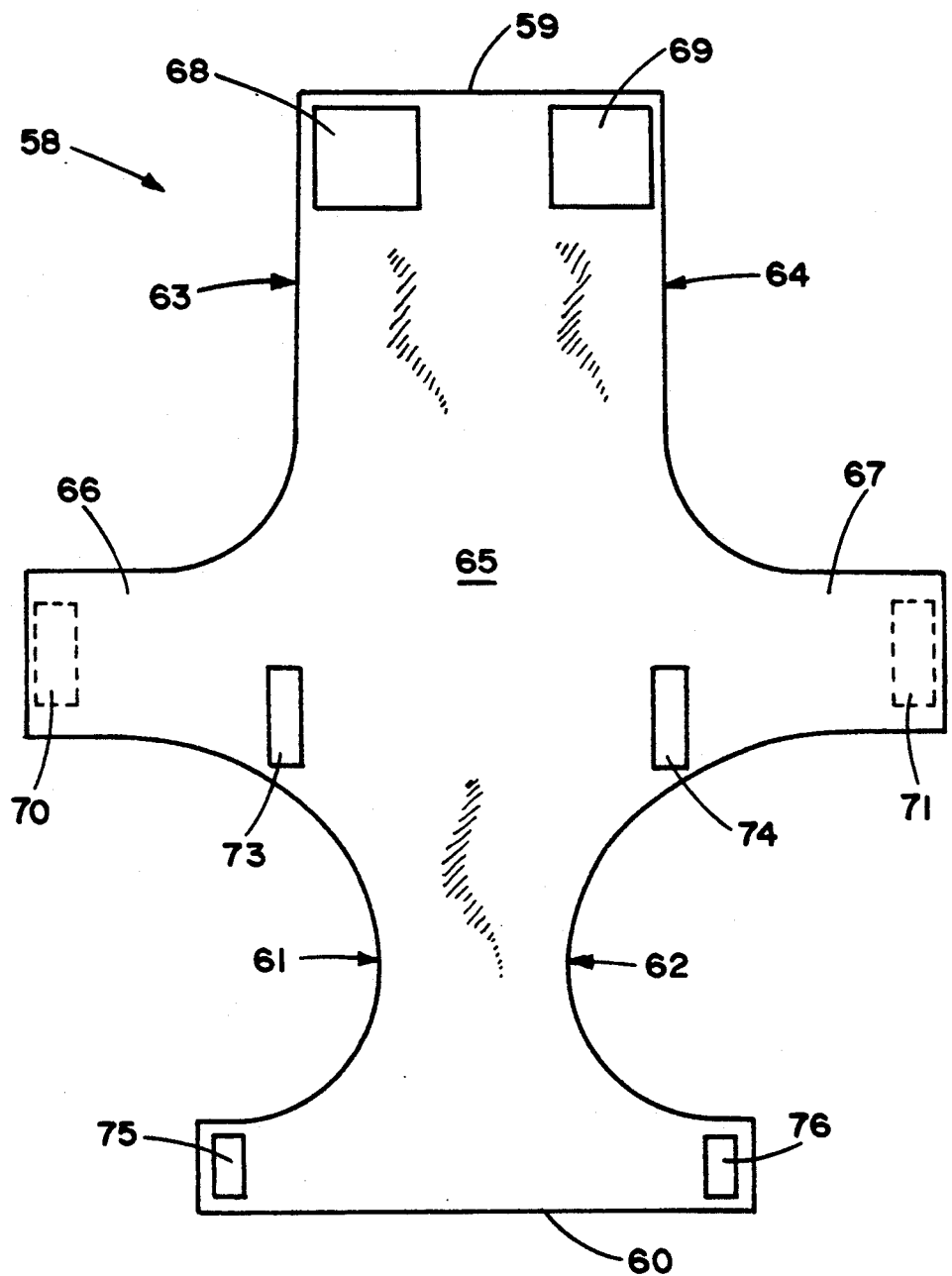
FIG. 2 is a top plan view of a preferred embodiment of the presently disclosed invention.
Figure 3:
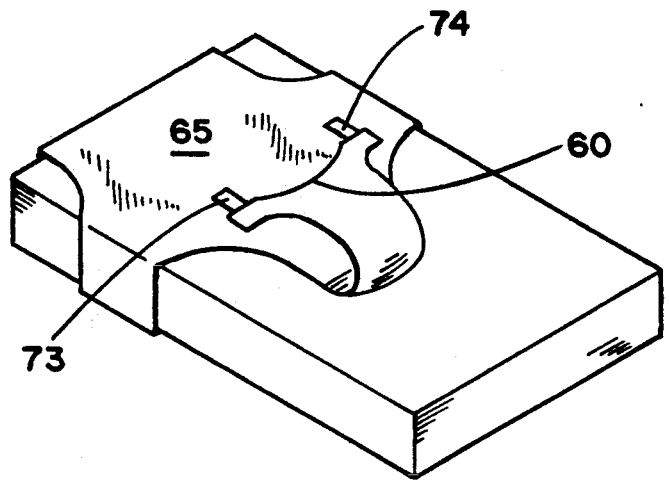
FIG. 3 is a perspective view of the device of FIG. 2 installed on a mattress and arranged in an infant-restraining configuration.

A preferred embodiment of the device is shown in FIG. 2 wherein the side edges intermediate the flared portions 66 and 67 and second end 60 of flexible sheet 58 are provided with indentations or cutouts 61 and 62 to reduce the bulk of sheet material passing between the legs of the infant. Firmly attached to infant-contacting surface 65 adjacent to first end 59 are patches 68 and 69 of releasable attachment means which cooperate with patches 70 and 71 secured to the mattress-contacting surface on flared portions 66 and 67 of side edges 63 and 64 to anchor the device to one end of a supporting mattress as depicted in FIG. 3. Cooperating patches 73 and 75 together with patches 74 and 76 of releasable attachment means hold folded end 60 in an infant-restraining configuration as also shown in FIG. 3.

Figure 4:
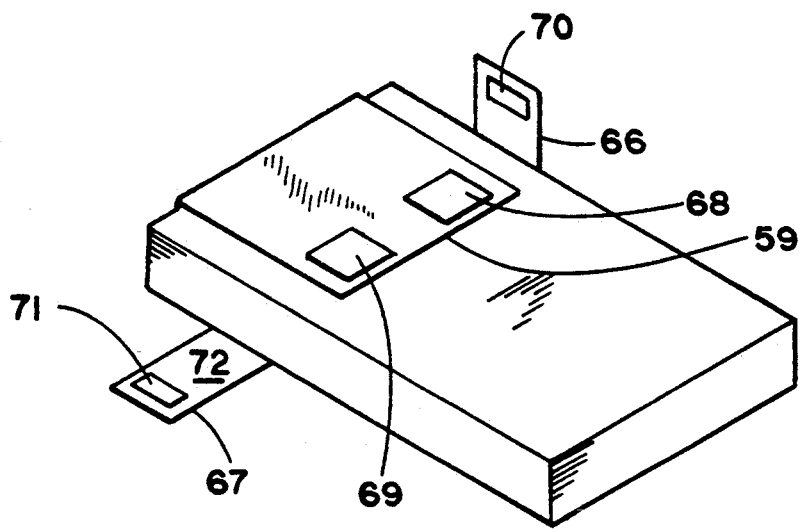
FIG. 4 is a perspective view of the underside of a mattress showing details of installation of the device of FIG. 2 on the mattress.
Figure 5:
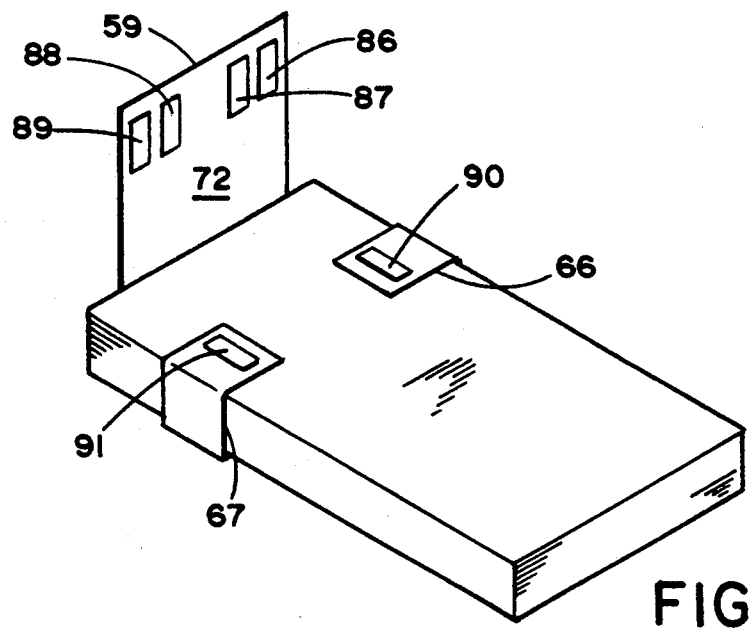
FIG. 5 is a perspective view of the underside of a mattress showing an alternative method of installing thereon the device of FIG. 2.

The patches of releasable attachment means which cooperate to anchor the restraining device to one end of a supporting mattress may be secured to either the infant-contacting surface or the mattress-contacting surface of flexible sheet 58. It is preferred that the patches adjacent to first end 59 be affixed to the infant-contacting surface of flexible sheet 58 while the cooperating patches disposed on flared portions 66 and 67 be affixed to the mattress-contacting surface 72 as shown in FIG. 4. This permits first end 59 to be held in position on the underside of the mattress while flared portions 66 and 67 are pulled snugly around each side of the mattress to bring patch 70 into contact with patch 68 and patch 71 into contact with patch 69. Patches 68 and 69 may also take the form of a plurality of smaller patches installed at spaced locations adjacent to first end 59 similar to that shown in FIG. 5. Alternatively, patches 86, 87, 88 and 89 (see FIG. 5) may be secured to the mattress-contacting surface 72 of flexible sheet 58 while patches 90 and 91 disposed on flared portions 66 and 67, respectively, are secured to the infant-contacting surface 65 of flexible sheet 58.

The patches of releasable attachment means used at various locations on the restraining device disclosed herein preferably comprise patches of VELCRO® which is a registered trademark for synthetic materials that adhere when pressed together. VELCRO® is also characterized as being a material comprising a large number of hook and loop fasteners. It is particularly desirable to employ VELCRO® patches on the infant-engaging end of the device (e.g., patches 73, 74, 75 and 76 in FIG. 2) to allow quick detachment of the joined patches in case of an emergency. The releasable attachment means used to anchor the restraining device to a mattress do not require quick detachment in emergency situations but even those attachment means preferably comprise VELCRO® materials due to the convenience and effectiveness of such materials in forming and maintaining a releasable attachment that holds the device in a snugly engaging relationship with the mattress.

Figure 6:
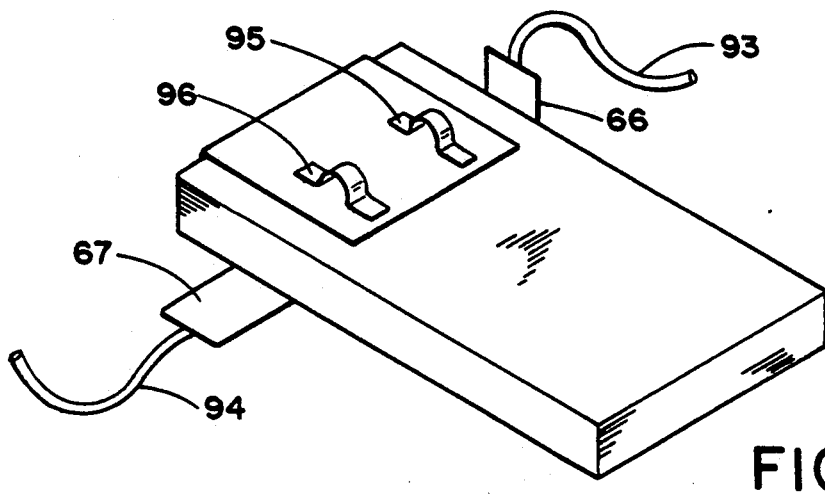
FIG. 6 is a perspective view of the underside of a mattress showing yet another method of installing thereon the device of FIG. 2.

Although VELCRO® is clearly preferred for providing the releasable attachment means used with the present invention, it will be appreciated that other releasable attachment means may be used. For example, FIG. 6 shows an arrangement wherein flared portions 66 and 67 have attached cords 93 and 94, respectively. Cord 93 is directed through loop 95 and cord 94 is guided through loop 96 before cords 93 and 94 are pulled snugly and are tied together. Alternatively, flared portions 66 and 67 and first end 59 may be provided with cooperating snaps, buttons and buttonholes, hooks and loops, etc. to provide means for releasably attaching flared portions 66 and 67 to first end 59 for anchoring the device to a supporting mattress.

Figure 7:
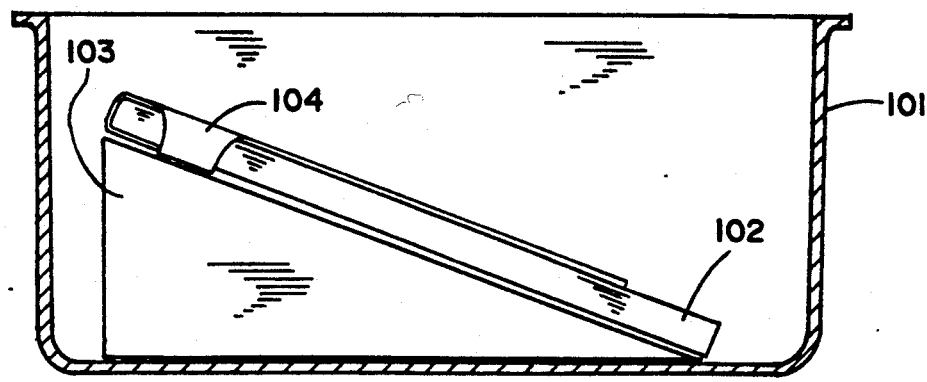
FIG. 7 is a side elevational view, partly in cross section, of a crib arrangement in which the presently disclosed device is used.

Shown in FIG. 7 is a typical arrangement employing the presently disclosed device. Open crib 101 contains mattress 102 supported by wedge 103. Installed on the elevated end of mattress 102 is infant restraining device 104. Although wedge 103 is manually placed beneath the mattress, it is obvious that other types of supports could be substituted for wedge 103 including those which employ mechanical or pneumatic devices to raise and lower one end of the mattress or the crib.

The infant restraining devices described here may be manufactured from various fabrics containing natural and/or synthetic fibers. The elongated flexible sheet from which the device is manufactured may be formed from a single type of fabric or a combination of fabrics. For example, the infant-engaging end may comprise a cotton fabric while the mattress-engaging end may comprise a fabric made from synthetic fibers with the two ends being joined by a suitable thread and resulting seam. The devices may also be formed from a plurality of fabric layers with or without a quilted construction. Thus, it is possible to manufacture a restraining device in which the mattress-contacting surface comprises a layer of fabric made from synthetic fibers while the infant-contacting surface comprises a layer of cotton fabric. By choosing fabrics and materials having suitable characteristics, a durable infant restraining device may be manufactured which has sufficient strength to hold an infant in a relatively fixed position when installed on a mattress.

It will be understood that a number of additional variations in the infant restraining device disclosed herein will be apparent to those skilled in the art. All such variations are deemed to be a part of the invention as defined by the scope of the appended claims.

What is claimed is:

1. In combination, a mattress for supporting an infant afflicted with gastroesophageal reflux, means for maintaining the mattress in an inclined position at angles up to 45 degrees, and an infant restraining device supported by said mattress and having one end of the device anchored to the elevated end of the mattress, said infant restraining device comprising a) an elongated flexible sheet having opposing first and second ends with one surface of the elongated flexible sheet being designated as the mattress-contacting surface and the opposite surface of the elongated flexible sheet being designated as the infant-contacting surface, said first end having a width no greater than the mattress width and being designed to wrap around the elevated end of the infant-supporting mattress with a sufficient length of said first end extending along the underside of the mattress for anchoring purposes and said second end of the elongated flexible sheet being designed to receive the infant placed on the mattress-supported restraining device, b) opposing first and second side edges disposed between said first and second ends with a portion of each side edge intermediate said first and second ends being flared a sufficient amount to permit the opposing flared portions to wrap around the respective opposing sides of the infant-supporting mattress and to overlap portions of said length of said first end of the elongated flexible sheet extending along the underside of the mattress, and c) means associated with said flared portions and the length of said first end of the flexible sheet extending along the underside of the mattress for adjustably and releasably attaching said first end of the flexible sheet to the flared portions of the opposing first and second side edges and thereby snugly engaging said elevated end of the infant-supporting mattress and anchoring the infant restraining device to the mattress.

2. The combination of claim 1 wherein said means for releasably attaching said flared portions to the length of said first end of the elongated flexible sheet extending along the underside of the mattress comprises cooperating patches of hook and loop fasteners strategically located on and secured to said elongated flexible sheet.

3. The combination of claim 2 wherein said patches of hook and loop fasteners are secured to the infant-contacting surface on said first end of the elongated flexible sheet and to the mattress-contacting surface of said flared portions.

4. The combination of claim 2 wherein said patches of hook and loop fasteners are secured to the mattress-contacting surface on said first end of the elongated flexible sheet and to the infant-contacting surface of said flared portions.

5. An improved infant restraining device adapted for use with an infant-supporting mattress and having improved means for anchoring the device to said mattress comprising a) an elongated flexible sheet having opposing first and second ends with one surface of the elongated flexible sheet being designated as the mattress-contacting surface and the opposite surface of the elongated flexible sheet being designated as the infant-contacting surface, said first end being designed to wrap around one end of the infant-supporting mattress with a sufficient length of said first end extending along the underside of the mattress for anchoring purposes and said second end of the elongated flexible sheet being designed to remain on top of the mattress and to pass between the legs of an infant placed on the mattress-supported restraining device, b) opposing first and second side edges disposed between said first and second ends with a portion of each side edge intermediate said first and second ends being flared outwardly a sufficient amount to permit the opposing flared portions to wrap around the respective opposing sides of the infant-supporting mattress and to overlap portions of said length of said first end of the elongated flexible sheet extending along the underside of the mattress c) means associated with said flared portions and the length of said first end of the flexible sheet extending along the underside of the mattress for adjustably and releasably attaching said first end of the flexible sheet to the flared portions of the opposing first and second side edges and thereby snugly engaging said one end of the infant-supporting mattress and anchoring the infant restraining device to the mattress, and d) means associated with said second end of the elongated flexible sheet for releasably attaching the second end to the sheet at a plurality of points on the sheet that are intermediate said first and second ends whereby the lower torso of an infant may be securely engaged when the second end of the flexible sheet is directed between the legs of the infant placed on said infant-contacting surface and is brought into contact with said plurality of points on the sheet that are intermediate said first and second ends.

6. The device of claim 5 wherein the width of the device adjacent to said first end of the elongated flexible sheet extending along the underside of the mattress is no greater than the width of the mattress on which the device is to be installed.

7. The device of claim 5 wherein said means for releasably attaching said flared portions to the length of said first end of the elongated flexible sheet extending along the underside of the mattress comprises cooperating patches of hook and loop fasteners strategically located on and secured to said elongated flexible sheet.

8. The device of claim 7 wherein said patches of hook and loop fasteners are secured to the infant-contacting surface of said first end of the elongated flexible sheet and to the mattress-contacting surface of said flared portions.

9. The device of claim 7 wherein said means for releasably attaching the second end to the sheet at said plurality of points on the sheet that are intermediate said first and second ends comprises cooperating patches of hook and loop fasteners strategically located on and secured to said elongated flexible sheet.

10. The device of claim 7 wherein said opposing first and second side edges intermediate said flared portions and said second end are provided with indentations for accommodating the legs of an infant restrained by the device.

11. The device of claim 7 wherein said elongated flexible sheet is a fabric formed from synthetic or cotton fibers.

12. The device of claim 7 wherein said elongated flexible sheet comprises a plurality of fabric layers.

13. An infant restraining device adapted for use with an infant-supporting mattress and having improved means for anchoring the device to said mattress comprising a) an elongated flexible sheet having opposing first and second ends with one surface of the elongated flexible sheet being designated as the mattress-contacting surface and the opposite surface of the elongated flexible sheet being designated as the infant-contacting surface, said first end being designed to wrap around one end of the infant-supporting mattress with a sufficient length of said first end extending along the underside of the mattress for anchoring purposes and said second end of the elongated flexible sheet being designed to receive an infant placed on the mattress-supported restraining device, b) opposing first and second side edges disposed between said first and second ends with a portion of each side edge intermediate said first and second ends being flared outwardly a sufficient amount to permit the opposing flared portions to wrap around the respective opposing sides of the infant-supporting mattress and to overlap portions of said length of said first end of the elongated flexible sheet extending along the underside of the mattress, and c) a plurality of cooperating loops secured to the infant-contacting surface of said first end of the elongated flexible sheet extending along the underside of the mattress and a flexible cord attached to each of said flared portions, said flexible cords being designed to pass through said plurality of cooperating loops secured to said first end of the elongated flexible sheet and to be tied together for anchoring the infant restraining device to the mattress.

* * * * *